United States Patent [19]

Nelson

[11] 4,276,475

[45] Jun. 30, 1981

[54] NOVEL PHOTOMETRIC SYSTEM

[75] Inventor: Kenneth E. Nelson, North Attleboro, Mass.

[73] Assignee: Waters Associates, Inc., Milford, Mass.

[21] Appl. No.: 30,312

[22] Filed: Apr. 16, 1979

Related U.S. Application Data

[60] Continuation of Ser. No. 734,082, Oct. 20, 1976, abandoned, which is a division of Ser. No. 625,590, Oct. 24, 1975, Pat. No. 4,011,451, which is a continuation-in-part of Ser. No. 592,941, Jul. 3, 1975, abandoned, which is a continuation of Ser. No. 470,076, May 15, 1974, abandoned.

[51] Int. Cl.³ .............................................. G01J 1/42
[52] U.S. Cl. .................................... 250/373; 250/435; 356/246
[58] Field of Search ............... 250/372, 373, 365, 343, 250/344, 345, 346, 432 R, 435; 356/181, 246, 427, 130

[56] References Cited

U.S. PATENT DOCUMENTS

| | | | |
|---|---|---|---|
| 2,547,212 | 4/1951 | Jamison et al. | 356/410X |
| 3,020,795 | 2/1962 | McKinney et al. | 356/246 |
| 3,591,801 | 7/1971 | Watson | 250/373 |
| 3,614,242 | 10/1971 | Hrdina | 356/410 |
| 3,666,941 | 5/1972 | Watson | 250/365 |
| 3,792,929 | 2/1974 | Alpert | 356/427 |

FOREIGN PATENT DOCUMENTS 40-14080  5/1965  Japan ........................ 250/343

Primary Examiner—Davis L. Willis

[57] ABSTRACT

Novel photometric apparatus advantageously having a conical shaped flow-cell comprising a light source proximate the narrow end and a photosensitive detector at the wider end of the cell. The flow-cell adequately compensates for a lens effect that has been discovered to be a substantial factor in electro-magnetic energy absorption studies on liquid streams.

11 Claims, 5 Drawing Figures

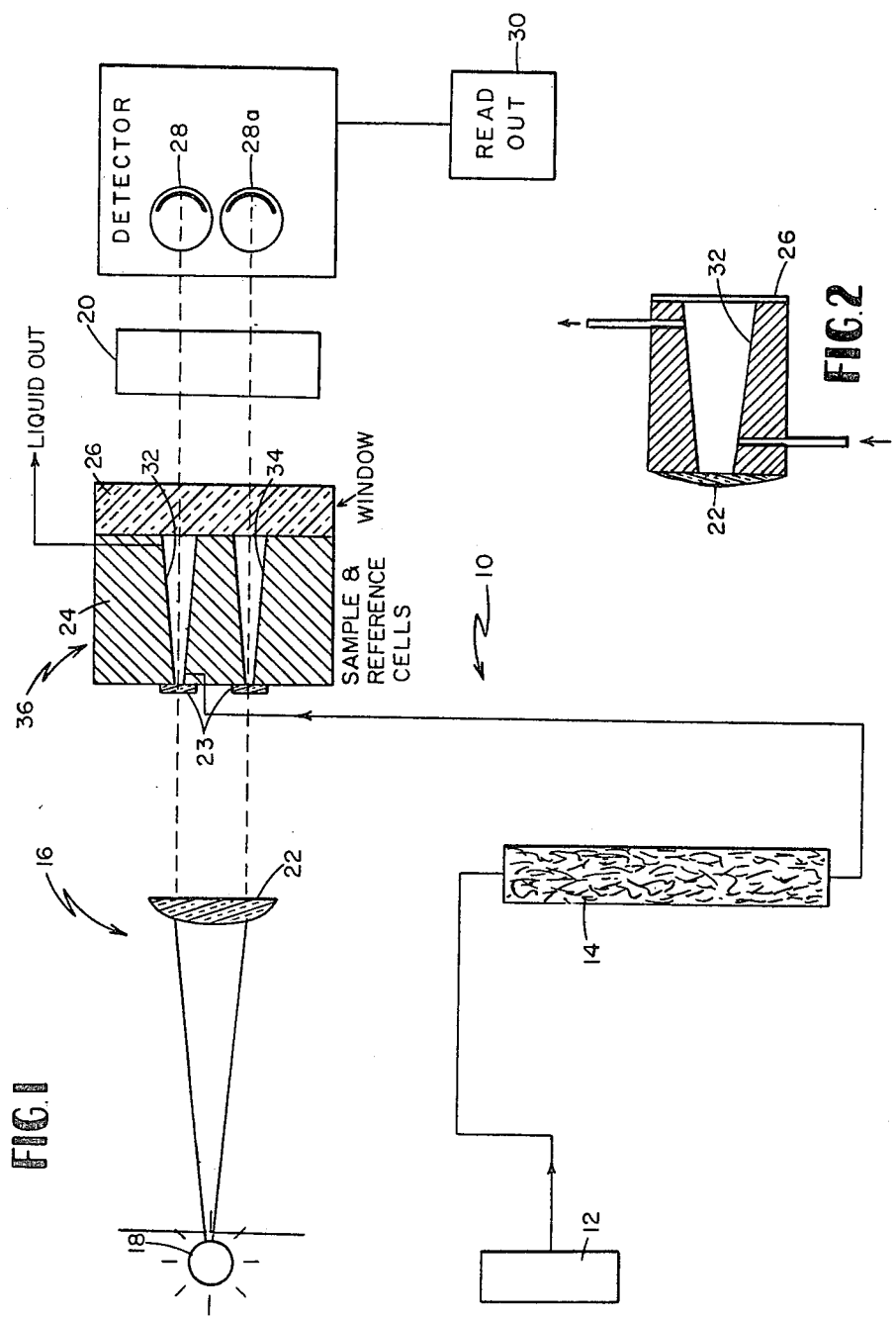

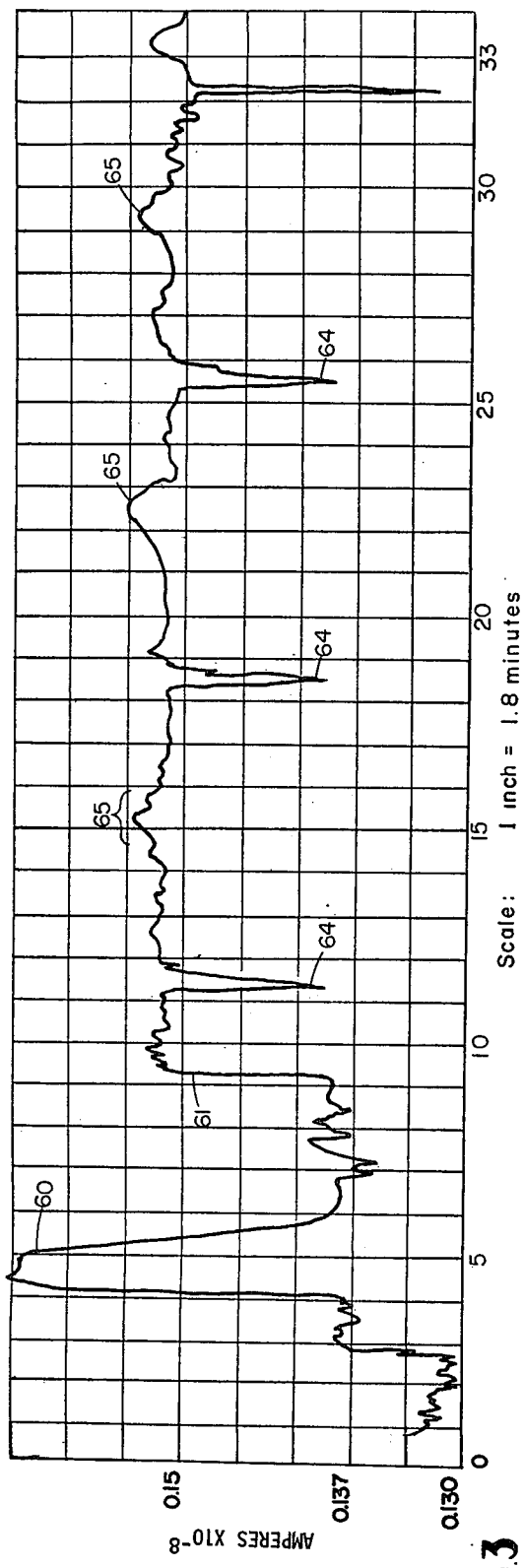
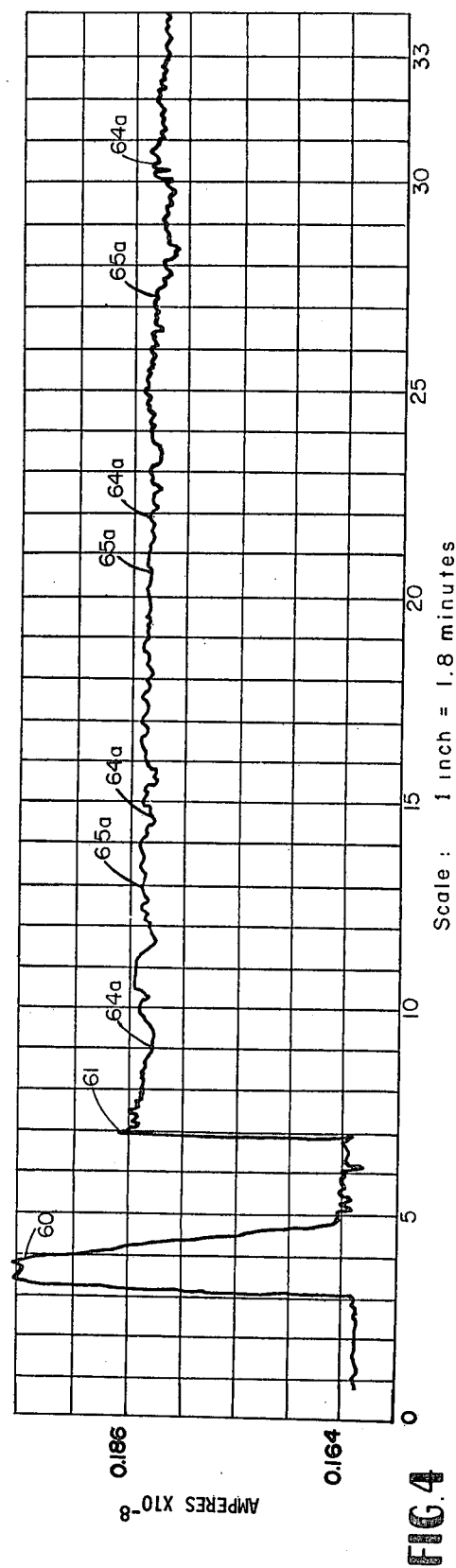

NOVEL PHOTOMETRIC SYSTEM

RELATED APPLICATIONS

This is a continuation of application Ser. No. 734,082, filed Oct. 20, 1976 now abandoned, which is a division of application Ser. No. 625,590, which was filed Oct. 24, 1975, and which issued Mar. 8, 1977, as U.S. Pat. No. 4,011,451. U.S. Pat. No. 4,011,451 is a continuation-in-part of Ser. No. 592,941 filed July 3, 1975, now abandoned, which was itself a continuation of Ser. No. 470,076 filed May 15, 1974, also abandoned.

BACKGROUND OF THE INVENTION

In analysis of very small quantities of liquids, it has been recognized that the physical conditioning of the fluid must be done very carefully. Thus, for example, in the field of liquid chromatography wherein very small, continuously-flowing streams of liquid are measured, care is taken to minimize mechanical and thermal disturbance of the liquid stream between the chromatographic column and analytical apparatus in which the liquid stream from the column is to be continuously analyzed. The primary objective is to present, to a transparent sample cell, the precise sequence of changing liquid composition that leaves the chromatography column.

The rationale and particulars of such apparatus are described in the art. For example, see U.S. Pat. No. 3,674,373 to Waters, Hutchins and Abrahams which involves a refractometer particularly well adapted to receive such a liquid stream. In general, the approach is to minimize the conduit path through which the liquid to be analyzed must travel and to provide a maximum thermal-conditioning of the liquid within such a minimized path. This generally illustrates the art-recognized importance of careful handling of sample liquid between its point of origin and the sample cell in which it is to be subjected to analysis, usually analysis which measures an effect of the sample liquid stream on some radiation directed into a flow-cell through which the stream passes.

Investigators have also realized that some attention must be given to the physical condition of the fluid even after it enters the flow-cell. Consequently, flow-cells have been made over smaller to avoid mixing and peak-spreading effects and, in some cases, a positive thermal equilibration of the cell with the liquid has been sought in order to avoid light-shimmering effects along the cell walls. Moreover, the cells are usually positioned with outlets so placed that any entrained gas bubbles tend to be carried upwardly out of the cell. It is noted that U.S. Pat. No. 3,666,941 to Watson describes a conical bifurcated cell wherein the larger end of the cell faces the light source, thereby forming means to gather a maximum amount of fluorescence-exciting radiation. Applicant's discovery, to be detailed below, is based upon a major improvement in flow-cell construction which solves a problem quite different than that described by Watson but which, like Watson's apparatus, is particularly useful in combination with liquid chromatography applications.

A recent patent, U.S. Pat. No. 3,792,929, to Alpert, it has been noted, seems to disclose a conical sample-holding cell. The patent related to static-sample devices and in no way involves fluid lenses of any type; although the patent came to the attention of the instant inventor after an error resulted in the word "field" appearing as "fluid" in the title of the Alpert patent. Moreover, the apparent and relative dimensions of the Alpert cell would not allow its effective use in most continuous-flow monitoring systems such as are encountered in liquid chromatographic work and the like.

SUMMARY OF THE INVENTION

A principal object of the invention is to provide an absorptometer which can be utilized with liquids of various refractive indices without encountering variations in optical performance of the instrument which will materially interfere with the quality of the absorption measurements being performed.

It is another object of the invention to provide an absorptometer wherein light entering the absorption cells is carefully processed before entry thereinto in order to avoid any such light's impinging on the walls of said absorptometer.

It is an object of the present invention to provide an improved liquid chromatographic system of the type utilizing a photometric analytical means.

It is a further object of the invention to provide a means for operating a photometric process whereby it is possible to minimize the size of sample volume of a flow cell without unduly affecting the performance of the photometer.

Another object of the invention is to provide a novel process of analyzing liquid by photometric method and a novel photometer for carrying out such analysis.

Another object of the invention is to provide a novel and improved sample-receiving flow-cell.

The above invention is based on the discovery that substantial spurious radiation signals are generated by differences in refractive indices and particularly by a lens-type effect caused by liquids of different refractive index and especially laminar-flow patterns at the interface of compositions differing in refractive index; the effect is troublesome in small cylindrical photometer sample-cells. These laminar flow patterns will sometimes be called "dynamic liquid lenses" in this description. In general the worst problems have been encountered in flow-cells in the microliter range, say flow-cells having a diameter of less than about 2 millimeters. In the usual situation the flow path of an ultra violet absorptometer cell is selected to be one centimeter in length, and a flow cell of 2 millimeters maximum diameter will have a volume of less than about 32 microliters. As the diameter increases the less effect caused by a given rate of laminar-flow tends to decrease; but a mere increase in diameter of a cylindrical flow path to avoid the lens effect is not practical because the increased diameter would result in either (1) a large increase in the volume of the tube or (2) a substantial decrease in length of the tube. A large increase in volume is untenable because the ability of the apparatus to detect very small samples would be substantially limited by dilution facts. The length of the cell cannot be markedly reduced without proportionately decreasing the magnitude of light absorbed by a given solution flowing through a cell. Still other conceivable tube configurations would give disadvantages liquid flow patterns.

Because the problem of these dynamic fluid lenses is primarily encountered at the point of changing compositions, its solution has been found to enhance both the quantitative and qualitative analytical capabilities of liquid chromatographic systems and like analytical systems where constantly changing compositions are inherent in the method. However, the apparatus is useful in other lens-inducing situations encountered in the process industry; e.g., where the dynamic fluid lens may be induced by temperature change or other phenomena that result in formation of a refractive index gradient within the flow-cell.

On discovering the nature of the problem associated with such small flow-cells, applicant has devised a simple constructional solution which substantially eliminates the problem: he has provided a flow-cell whereby the lens effect is rapidly dissipated by a progressive increase in the cross-sectional area of the flow-cell along the flow path. Thus, the wall of the flow-cell advantageously forms a diverging surface of rotation whereby the walls form an angle of divergence of at least about one angular degree with the axis of the cell. An optical system is advantageously provided which avoids any substantial radiation from entering the cell at sharp angles which would result in the radiation to impinge on the walls of the cells. An angle of about 1.5 degrees or slightly greater provides sufficient widening to substantially dissipate the undesirable effect of the dynamic liquid lens formed at the interface of water and most organic solvents. The improvement is largely achieved by collecting refracted light, which would have otherwise been absorbed on the wall of the cell, but it is also believed the reduction in velocity of the stream during its transit through the cell—usually a reduction of over 50%—causes a dissipation of the lens effect itself which reduces the amount of refracted light directed against the walls of the cell. Angles of divergence between the axis of the flowpath and the wall of the cell of 1° to 3° are most advantageous; larger angles only become problems because they usually dictate a larger cell size.

In liquid chromatographic applications, best results will be achieved if the apparatus to be used with the flow-cell is selected to achieve the most ideal flow pattern possible, i.e., the flow pattern most nearly achieving plug flow. This is true of all flow in a liquid chromatographic system: flow from sample injection to the column and flow between the column and the analytical component of the system. Such apparatus is available: an injection advantageously used is that available under the trade description Model U6K Injector by Waters Associates, Inc. A pumping system, advantageously used to feed liquid into a high pressure column, is that available from the same source under the trade designation Model 6000 Solvent Delivery System. However, as will be obvious to those skilled in the art, other such apparatus will be generally useful in many applications in which the instant invention is advantageously used.

It will also be obvious to those skilled in the art that a number of modifications can be made in the shape of the wall structure of the flow-cell. For example, further enlargement of the cell conduit over that defined minimal conical shape will yield an operable cell that will avoid the effect of the dynamic liquid lens but will also be larger in size and therefore less favorable for many applications. Such enlargement is nonfunctional with respect to the present invention. However other such shapes including such as catenoidal horns, hyperbolic horns, parabolic and hyperbolic surfaces as well as similar surfaces of revolution are all intended to be covered by the term "generally truncated cone" as used in this application. Such shapes may on some occasions be favorable in view of effects caused by special flow properties of the fluid components which form the dynamic lens, temperature profiles across the cell, friction effects along the surface of the wall or the like. "Generally conical", therefore, is meant to include any flow-cell wherein the inlet port is smaller than the outlet port and the cross section of the cell is progressively larger as measured closer to the outlet port.

It is to be realized that the most important structural aspect of the invention relates to the relationship of the conical cell to the direction of the lightpath: the larger end of the cone must be toward the detector. It is possible, however, to reverse the direction of flow of the liquid to be analyzed through the cell. Best practice is to avoid this situation or, if for some reason it is desirable, to arrange the attitude of the cell so that any minute gas bubbles can be displaced upwardly toward the outlet port of the cell.

In chromatographic related analytical operations and other such operations which monitor microliter quantities of a flowing sample, the length-to-average diameter ratio of the flow cell is advantageously at least 5 to 1. It is primarily the monitoring of such small samples, rather than inherent optical considerations, which make angles of divergence greater than 3° undesirable for many applications.

One additional advantage of the apparatus disclosed herein is that fact that, for some applications, it allows the light source to be brought (physically, or by optical means) closer to the sample cell without undue losses of light by refraction and light scattering occuring primarily at the interfaces of gas-lens and liquid-lens interfaces.

Although, the above invention has been described largely in terms of flow cells, it should be recognized that it also has advantage in non-flow cell situations wherein liquids of substantial difference in refractive index are used with the same optical system.

ILLUSTRATIVE EXAMPLE OF THE INVENTION

In this application and accompanying drawings there is shown and described a preferred embodiment of the invention and suggested various alternatives and modifications thereof, but it is to be understood that these are not intended to be exhaustive and that other changes and modifications can be made within the scope of the invention. These suggestions are selected and included for purposes of illustration in order that others skilled in the art will more fully understand the invention and the principles thereof and will be able to modify it in a variety of forms, each as may be best suited in the condition of a particular case.

IN THE DRAWINGS

FIG. 1 is a schematic diagram of an analytical apparatus constructed according to the invention.

FIG. 2 is a section of a flow-cell constructed according to the invention.

FIG. 3 is a graph illustrating the output signal of an ultra-violet absorption-measuring apparatus using a conventional cylindrical flow-cell.

FIG. 4 is a graph illustrating a chart similar to that shown in FIG. 3 but obtained utilizing a flow-cell constructed according to the invention.

Figure 5:
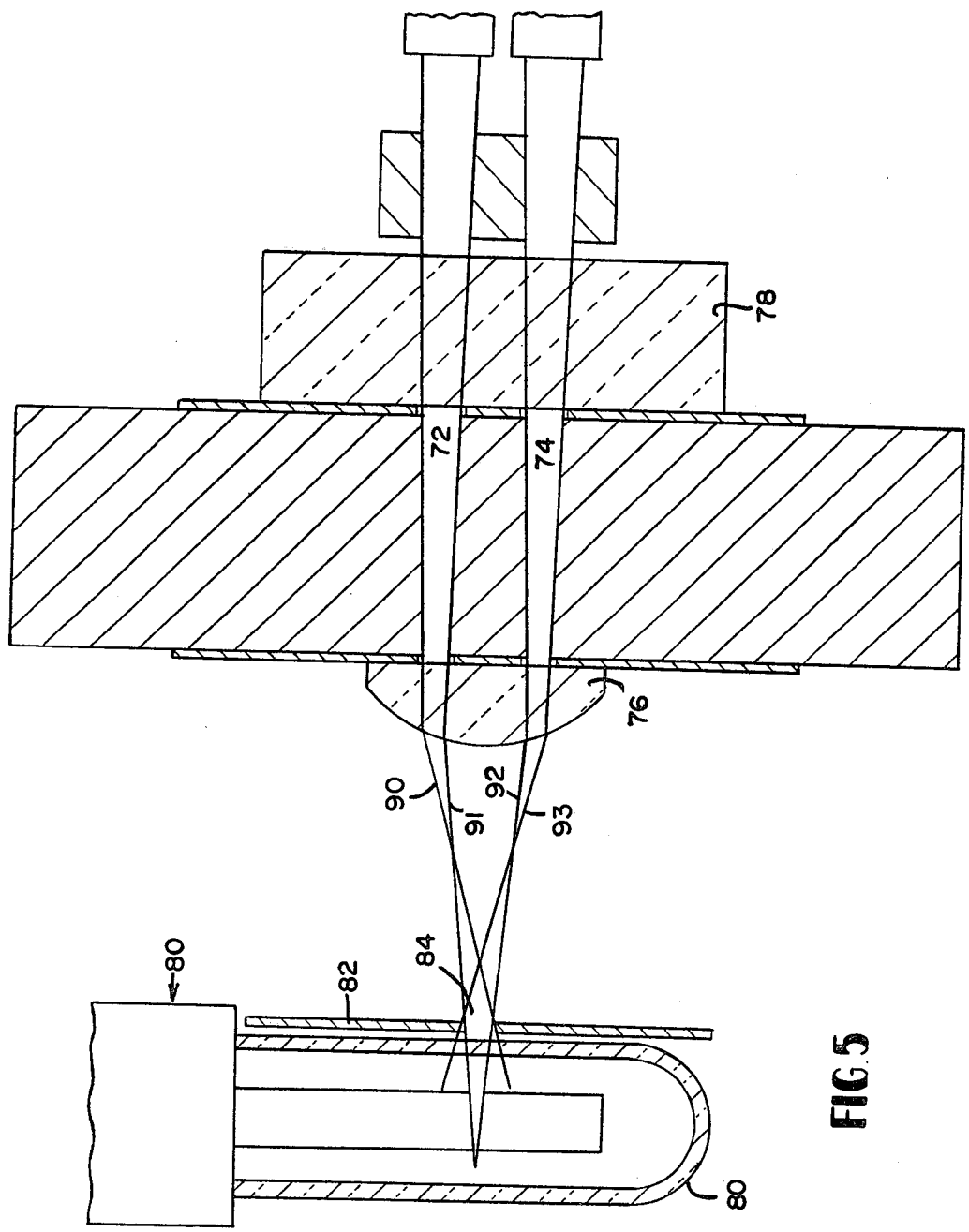
FIG. 5 is another schematic diagram showing a particularly advantageous mode of the invention.

FIG. 1 illustrates an analytical system 10 comprising a source 12 of a liquid to be analyzed, a liquid chromatography column 14, and an ultra-violet absorbtometer 16 comprising a light source 18, an interference filter 20, a lens system 22, front windows 23, main housing wall of a sample cell 24, a rear window 26 and photoelectric detector 28. Signals from photo detector 28 and a reference detector 28a are processed according to known techniques to provide a suitable electronic signal which may be used as a control means or as is more frequent, to provide a visible recording on a recorder means 30.

An important feature in FIG. 1 is the sample cell 24 which incorporates the conical flowpath 32. However, this innovation directly enhances the performance of the entire system by providing means to take the liquid output from chromatographic column 14 and process it in the ultra-violet absorption apparatus so that the resulting light reaching detector 28 is substantially free of detrimental loss of light due to the influence of dynamic liquid lenses.

In the apparatus of FIG. 1, the light source is rated at 2.4 watts and has principal wave length of 253.7 nanometers. The volume of the sample cell, best seen in FIG. 2, is about 12.5 microliters: it is about 0.04 inches in diameter at the inlet end, about 0.06 inches in diameter at the outlet end and about 0.394 inches in length. A reference flow-cell 34 is positioned within cell assembly 36, as is common in the photometric analysis of liquids. This cell may be empty, full of a stagnant liquid or have a flowing reference fluid therein.

FIG. 3 illustrates graphically the type of detection problem which can be encountered in radiation-absorption analysis because of interference in ultra-violet transmittance by dynamic liquid lens as they move through a thin cylindrical sample cell.

In each of FIGS. 3 and 4, there is an initial peak 60 caused by a calibration fluid—a standard dichromate solution flowing through the cells at a rate of one milliliter per minute. The next rise 61 in each curve, is merely an adjustment of the zero level of the recorder. At this point, each curve has a relatively flat reference level indicative of the low ultra-violet absorption of water.

This reference level is flat for the continuous feed in FIG. 3 but interrupted by abrupt drops in light transmission when injections of aqueous methanol solution are introduced into the column. These apparent increases absorptivity in absorption are caused by the refraction from dynamic fluid lens formed by the methanol-water interface and the interfaces of various mixtures thereof. Once refracted, a substantial portion of light is absorbed on the parallel walls of the conventional flow-cell.

The valleys 64 of FIG. 3 illustrate the effect caused by a transition from water flow of 0.3 ml/minute to a flow of 0.3 ml per minute of a 10% aqueous solution of methanol. This solution is added through a sample loop over a period of about 3.3 minutes. Then, as water returns flushing the loop, there is an upward displacement 65 of the curve caused by the dynamic liquid lens now being formed of the water flush flowing behind the methanol solution. After the flushing with water is completed, fluid-lens induced displacement subsides until another injection of water-methanol solution is started.

Equivalent injections made in the same system, except for the use of a flow-cell as shown in FIG. 2 result in no reduction in transmission, when methanol is added. Nor is there any substantial increase in transmission when the water flush occurs. Such points are identified as 64a and 65a in FIG. 4.

An advantageous means for assuring that the light entering the cells does not refract against the walls is disclosed in FIG. 5 and comprises an aperture serving to mask the light source at a point between the source and the flow cell structure itself. This pre-masking procedure assures that no light entering the cell from a large source can be refracted at such an angle as to impinge on the tapered walls of the cell. Another advantage of the apparatus shown in FIG. 5 is to combine the lens and front window of the cell. This procedure allows one to minimize the distance between the light source (aperture) and the flow cell thereby providing a more efficient use of light generated in the absorptometer apparatus.

FIG. 5 illustrates a plan view flow cell assembly 70 comprising conical reference cell 72 and sample cell 74. Sample cell 74 is usually equipped with a flow inlet and outlet ports as described in FIG. 1. The ports are not shown in FIG. 5 to leave cells appearing as unencumbered as possible. The front wall and back wall of the cell assembly are formed of lens 76 and window 78. The light entering the cells originates at ultraviolet lamp 80. A mask 82 comprises a means to intercept light from source 80 that would be undesirable were it to reach the cells 72 and 74. Light passing through aperture 84 in mask 42 is so masked that the extreme light rays enter either light cell so that they cannot be refracted at an angle which would allow them to impinge upon the tapered walls of the cells by any commonly used liquid.

It has been found desirable and convenient to use lens 22 as a window. This procedure allows the aperture 84, and consequently the lamp 80 to be placed closer to the sample cell.

In a typical arrangement as shown in FIG. 5, the axis of the cells are spaced apart by 0.160 inch, the lens has an edge thickness of 0.04 inch; the radius of curvature of the lens is 0.2559 inch; the mask and aperture are spaced 0.58 inch from that edge of the lens nearest entrance to cells 72 and 74; the aperture is 0.044 inch. The length of each cell is 0.394 inches, the diameter of the front aperture of the cells is 0.040 inches, and this tapers to 0.060-inch rear aperture.

The lower edge of aperture 84 of masking means 82 effectively masks any potential light ray, beyond limiting ray 90, from approaching lens 76 at such an angle that it will be diverted by lens 76 into hitting the upper (looking at FIG. 5) wall of cell 72. Similarly the upper edge of aperture 84 effective masks any light ray, beyond limiting ray 93, from approaching lens 76 at such an angle that it will be diverted into hitting the lower wall of cell 74.

Substantially all of the light entering the cells is either absorbed in the liquid or transmitted through the cell and thus made available for measurement by the light detector 28. It will be understood that a light filter 20 is sometimes used to filter out waves lengths of light which are not to be measured. In this sense, the filter is merely that part of the detector apparatus which selects what pre-selected quality of light is to be allowed to reach the photo-sensitive elements thereof.

It will be noted that optimum practice of the invention will include use of a flow cell, the crossection of which is enlarged from the end which the light enters towards the end which light leaves. Such a tapered configuration reduces unnecessary flow cell volume, and this is believed to be an important factor in many applications, e.g. wherein very small samples are being studied and wherein ancillary apparatus is selected to avoid gross peak spreading before the liquid enters the absorbtometer. However, where one is willing to tolerate the disadvantages of a flow cell which is somewhat larger than required, the advantages of using an apertured mask to control a cone of light entering the cell and consequently avoid incidence of light on any portion of the walls of reference cell and sample cell would still be considerable whether or not the cell were tapered.

It is stressed that it is intended to cover the apparatus of the invention, whether or not it exists in non-assembled parts, wherein some intrinsic or extrinsic system is so related to such parts that the system facilitates the collection of the parts for assembly at a particular place or places. Such a system could include co-ordinated shipping instruction, a coordinated parts-packaging system, assembly instructions or any other system which facilitates assembly of apparatus into a functioning system as defined in claims explicitly relating to assembled systems.

It is to be understood that the following claims are intended to cover all of the generic and specific features of the invention herein described and all statements of the scope of the invention which might be said to fall therebetween.

What is claimed is:

1. Apparatus for measuring the amount of light absorbed by a portion of a flowing liquid, comprising:
   a sample cell for transporting said flowing liquid along the longitudinal dimension of said cell, said cell including
      a wall extending generally longitudinally,
      a light entrance window at one longitudinal end of said cell, and
      a light exit window at the other longitudinal end of said cell;
   a light source for generating a light beam;
   masking means including a mask with an aperture positioned between said light source and said entrance window of said cell for optically shaping said beam so that the portion of said beam that enters said cell through said window is transmitted through said cell without contacting said cell wall for a predetermined maximum liquid-lensing condition, thereby assuring that wall contact does not occur under any expected condition,
   said maximum condition corresponding to when the liquid in said cell has a distribution of refractive index that causes the greatest expected divergent spreading of said beam by refraction,
   detection means positioned beyond said exit window for measuring substantially all of the light emerging from said window, said detection means including a photoelectric element onto which said emerging light beam is incident,
   whereby the amount of light detected by said apparatus is independent of the amount by which said beam is bent by refraction within said cell because all of said beam entering said cell and not absorbed by said liquid also emerges from said cell and is detected, thereby making said apparatus independent of variations in the refractive index of said liquid.

2. The apparatus of claim 1 further comprising a second cell for holding a reference liquid, said second cell including a wall and entrance and exit windows, said masking means including means to shape said beam so that the portion of the beam entering said second cell is transmitted therethrough without contacting the cell walls, and said detection means including means for measuring substantially all light emerging from said second cell.

3. The apparatus of claim 1 wherein said sample and reference cells have parallel longitudinal axes and said light entrance windows of said cells each include a lens surface for bending said beam emerging from said mask into the general direction of parallel cell axes.

4. The apparatus of claim 3 wherein said entrance windows comprise a single element and said lens surfaces are a common surface on said element.

5. The apparatus of claim 1 wherein
   said mask is positioned with respect to said light source and said aperture is sized so that light emerges from said aperture at less than a predetermined angle with respect to the longitudinal centerline of said cell and
   said cell is shaped so that light entering said cell with an inclination of no more than said predetermined angle passes through said cell without contacting said cell wall, for said predetermined liquid-lensing condition.

6. The apparatus of claim 5 wherein said mask is substantially closer to said light source than to said cell.

7. The apparatus of claim 1 wherein said masking means includes means for shaping said beam so that light of a pre-selected wavelength that enters said cell through said window is transmitted through said cell without contacting said cell wall for said predetermined liquid-lensing condition.

8. A photometer as defined in claim 1 wherein said light source and said measuring means are so selected that said photometer is an ultra-violet absorbance detector.

9. A photometer as defined in claim 1 wherein said sample has a volume of less than 32 microliters and a maximum diameter of less than 2 millimeters.

10. A photometer as defined in claim 8 wherein said sample cell has a volume of less than 32 microliters and a maximum diameter of less than 2 millimeters.

11. A photometer as defined in claim 8 wherein said flow cell comprises walls devergent at an angle of at least 1° from the axis of said flowpath.

* * * * *

UNITED STATES PATENT AND TRADEMARK OFFICE
CERTIFICATE OF CORRECTION

PATENT NO. : 4,276,475
DATED : June 30, 1981
INVENTOR(S) : Kenneth E. Nelson

It is certified that error appears in the above—identified patent and that said Letters Patent is hereby corrected as shown below:

Column 2, line 49, "the less effect" should read

-- the lens effect --.

Signed and Sealed this

Twenty-second Day of September 1981

[SEAL]

Attest:

Attesting Officer

GERALD J. MOSSINGHOFF
Commissioner of Patents and Trademarks